United States Patent
Ramanathan

(10) Patent No.: US 11,361,257 B2
(45) Date of Patent: Jun. 14, 2022

(54) METHOD AND SYSTEM FOR MANAGING DIAGNOSTIC IMAGING ORDERS

(71) Applicant: RAMSOFT Inc., Toronto (CA)

(72) Inventor: Vijay Ramanathan, Toronto (CA)

(73) Assignee: RAMSOFT Inc., Toronto (CA)

( * ) Notice: Subject to any disclaimer, the term of this patent is extended or adjusted under 35 U.S.C. 154(b) by 1007 days.

(21) Appl. No.: 15/978,009

(22) Filed: May 11, 2018

(65) Prior Publication Data

US 2018/0330286 A1   Nov. 15, 2018

Related U.S. Application Data

(60) Provisional application No. 62/504,983, filed on May 11, 2017.

(51) Int. Cl.
| | |
|---|---|
| *G06Q 10/06* | (2012.01) |
| *G16H 30/20* | (2018.01) |
| *G16H 40/20* | (2018.01) |
| G16H 30/40 | (2018.01) |
| G16H 70/20 | (2018.01) |

(52) U.S. Cl.
CPC ............ *G06Q 10/06* (2013.01); *G16H 30/20* (2018.01); *G16H 40/20* (2018.01); *G16H 30/40* (2018.01); *G16H 70/20* (2018.01)

(58) Field of Classification Search
CPC .................................. G06F 10/06; G06Q 10/06
See application file for complete search history.

(56) References Cited

U.S. PATENT DOCUMENTS

| | | | | |
|---|---|---|---|---|
| 6,915,254 | B1 * | 7/2005 | Heinze ................... | G06F 40/20 704/9 |
| 8,265,952 | B1 * | 9/2012 | Smith .................... | G16H 40/20 705/2 |
| 2002/0147616 | A1 * | 10/2002 | Pollard .................. | G06Q 10/10 705/3 |
| 2012/0330707 | A1 * | 12/2012 | Loucks .................. | G06Q 10/06 705/7.13 |
| 2013/0173308 | A1 * | 7/2013 | Hough ................... | G16H 40/67 705/3 |

(Continued)

FOREIGN PATENT DOCUMENTS

WO   WO-2017184176 A1 * 10/2017   ............... G06N 5/02

OTHER PUBLICATIONS

Massat, M. B. (2017). Implementing clinical decision support for advanced medical imaging studies. Applied Radiology, 47(1), 18(3). Retrieved from https://dialog.proquest.com/professional/docview/1881885919?accountid=131444 (Year: 2017).*

*Primary Examiner* — Robert A Sorey
(74) *Attorney, Agent, or Firm* — Sheppard Mullin Richter & Hampton LLP

(57) ABSTRACT

Methods and systems are described for managing diagnostic imaging order requests. A system is configured to receive diagnostic image order request from ordering physicians. The received diagnostic imaging order requests comprise imaging order information including ordering provider information, patient information, diagnostic imaging order information, and/or clinical decision support information. Upon determining that a guideline-based clinical decision support system process was required but not followed, a notification to the ordering physician is generated and sent.

20 Claims, 7 Drawing Sheets

(56) References Cited

U.S. PATENT DOCUMENTS

| | | | |
|---|---|---|---|
| 2015/0278463 A1* | 10/2015 | Tolle ..................... | G06F 16/51 |
| | | | 705/4 |
| 2017/0116373 A1* | 4/2017 | Ginsburg ............... | G16H 10/40 |
| 2017/0199979 A1* | 7/2017 | Reiner ................... | G16Z 99/00 |

* cited by examiner

Fig. 3B

```
MSH|^~\&|RAMSOFT|SENDING FACILITY|RAMSOFT|RECEIVING FACILITY|20101223202939-0400||
ORM^O01|104|P|2.3.1||||||| UNICODE UTF-8||
EVN|O01|20101223202939-0400||||
PID||P12345^^^ISSUER^MR|P12345^^^ISSUER^MR||PATIENT^TEST^M^^^||19741018|M||2106-3^
WHITE^HL70005|10808 FOOTHILL BLVD^^RANCHO CUCAMONGA^CA^91730^US||(909)481-5872^^^qa@ramsoft.com|(909)481-5800x1||M||12345|286-50-8510|||2135-2^
HISPANIC OR LATINO^HL70189|
PV1||O|ER^ER^^MEDICAL CENTER^^^^^ER||||1234567890^JONES^SAMUEL^^MD^|1234567890^JONES^SAMUEL^^MD^|306507^SMITH^JOHN^^MD^~669789^JONES^ED^^MD^|||||||||||||||||||||||||||||||||||||||
ORC|SC|A123456|A123456||SC||1^^^20110615025434-0400^^R^^^^||20110704211036-0400|
FRONTDESK||1234567890^JONES^SAMUEL^^MD^|^^MEDICAL CENTER|8883439146||MEDICAL CENTER|
OBR||A123456|A123456|70100^XRAY JAW < 4 VIEWS^^^||20110704211036-0400|||||R|
Patient was in an altercation||^^^JAW^|1234567890^JONES^SAMUEL^^MD^||A123456|67890|A123456||||CR|||^^^20110615025434-0400^^R^^^^||WALK|830.1^DISLOCATION OF JAW; OPEN DISLOCATION^|
1345678901&PATEL&APU&&MD&||&LEVINSON&KERRY&K&RT&|&FRANKLIN&KATY&R&&||||PATIENT WAS DRUNK||O|||70100^XRAY JAW < 4 VIEWS^^^||
OBX|1|ST|^BODY HEIGHT||1.69|m||||F|||||
OBX|2|ST|^BODY WEIGHT||75|kg||||F|||||
OBX|3|ST||||||||||||
OBX|4|CE|5515-6^REQUESTED PROCEDURE IS APPROPRIATE^LN|1|CODE^NAME OF AUC CONTENT PROVIDER^HEALTH PROVIDERS AUC|||||O|N469|20151027155700|||98234.22.1||||1.2.840.5677912.454.66.78.9.9.0.1233
NTE|1|O|ACME CDS System v1.0, XYZ Hospital, 1.2.840.5356356345.3454245.245234523
IN1|1|89765|BCBS|BLUE CROSS BLUE SHIELD|1 SUNSET BLVD^^BEVERLY HILLS^CA^90210^US|^^^^^|
(213)555-5555|8412345|||RAMSOFT|20101006||||PATIENT^TEST^M^^^|SEL|19741018|10808 FOOTHILL BLVD^^RANCHO CUCAMONGA^CA^91730^US||||||||||||||||||1|M|
9480 UTICA AVE^^RANCHO CUCAMONGA^CA^91730^US|||||89765|
|
```

METHOD AND SYSTEM FOR MANAGING DIAGNOSTIC IMAGING ORDERS

CROSS-REFERENCE TO RELATED APPLICATIONS

This application claims priority to U.S. Provisional Patent Application No. 62/504,983 filed on May 11, 2017, which is incorporated herein by reference in its entirety.

TECHNICAL FIELD

The present disclosure relates generally to systems for managing diagnostic imaging orders. More particularly, some embodiments relate to systems and methods for confirming a guideline-based clinical decision support system (CDSS) was consulted on diagnostic imaging orders.

BACKGROUND

In the hospital environment, imaging data may be captured by medical imaging systems. The images may be created using many existing methods, including radiography, or X-ray imaging, computed tomography (CT), magnetic resonance imaging (MRI), ultrasound, mammography, nuclear medicine, positron emission tomography (PET), and other modalities.

Section 218(b) of the Protecting Access to Medicare Act of 2014, amended Title XVIII of the Social Security Act, by including section 1834(q) which directs Centers for Medicare & Medicaid (CMS) to establish a program to promote the use of appropriate use criteria (AUC) via electronic clinical decision support (CDS) for advanced diagnostic imaging services. This new program, scheduled to take effect Jan. 1, 2018, will require an ordering physician to consult a guideline-based clinical decision support system (CDSS) system prior to submitting an order for advanced imaging to a radiology center or hospital. Pursuant to this requirement, Medicare will deem advanced imaging studies ineligible for payment absent proof that CDS was followed by the ordering physician.

A CDSS may help to quickly determine what type of an imaging exam or diagnostic testing is needed for a patient with specific symptoms. Consulting criteria-based system such as a CDSS may enable physicians to order the right imaging examination at the right time, reduce unnecessary scans, and lower imaging costs. Ordering physicians, however, do not always consult a CDSS when making imaging orders. Moreover, it is the imaging facility and rendering provider (e.g., radiologist) that may be denied payment for services if the ordering physician does not fulfill CDS requirements. Inability to confirm whether or not a CDSS was consulted for a particular imaging order may increase imaging costs and unnecessarily burden imaging service providers by denying reimbursement on orders submitted without consulting a clinical decision support mechanism.

Although imaging service providers may deny imaging orders that provide no indication of consulting a CDSS, this may result in unnecessary delays having a direct impact on patient care. Moreover, inability to timely contact an ordering physician to obtain a confirmation that a CDSS was consulted may further these delays.

Accordingly, improved methods and systems receiving and processing diagnostic imaging orders, particularly those that require a referring physician to perform CDS, are needed.

BRIEF DESCRIPTION OF THE DRAWINGS

The figures are provided for purposes of illustration only and merely depict typical or example embodiments. They do not limit the breadth, scope, or applicability of the invention.

FIG. 3B illustrates an example HL7 Order Message with extracted data fields highlighted.

DETAILED DESCRIPTION

Embodiments disclosed herein are directed to systems and methods for receiving and processing diagnostic imaging orders. Particularly, embodiments disclosed herein are directed to a system and method for receiving diagnostic imaging order dataset (e.g., an HL7 order message dataset), extracting information from the dataset to determine if CDS is required and was performed by an ordering provider, and providing a notification and interface for the diagnostic imaging ordering provider to perform CDS if CDS was required and not performed.

Figure 1:
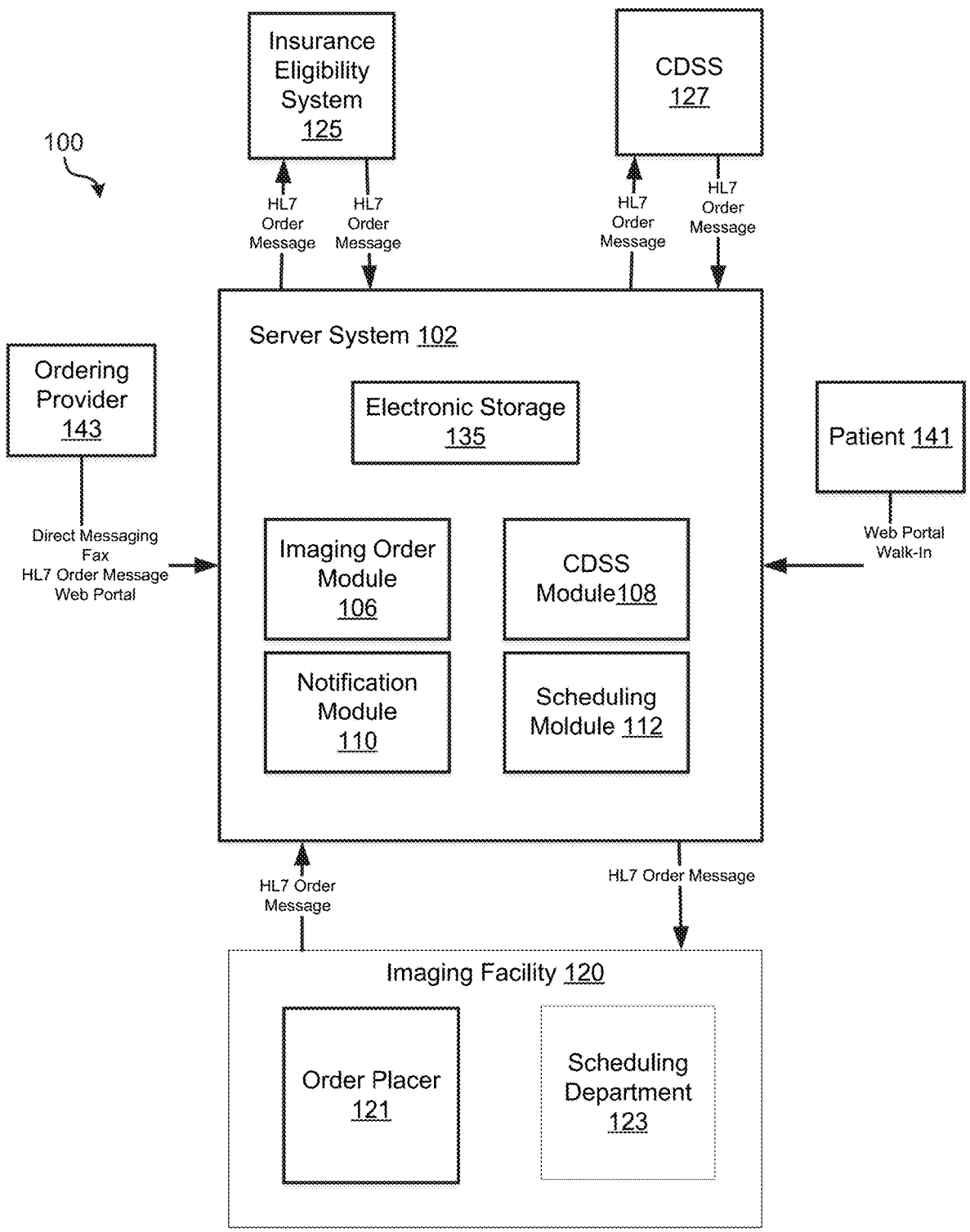
FIG. 1 illustrates an example diagnostic imaging order management environment for implementing the systems and methods of the present disclosure, in accordance with one or more implementations.

FIG. 1 illustrates an example diagnostic imaging order management environment 100 in which the systems and methods of the present disclosure may be implemented. As illustrated in FIG. 1, environment 100 may include at least one server system 102 configured for diagnostic imaging order management. System 102 may include at least one or more servers, one or more client computing platforms, and/or other modules. A server of system 102 may be configured to communicate with one or more client computing platforms according to a client/server architecture. The users of system 102 may access system 102 via a client computing platform.

Server system 102 may include one or more physical processors, and/or other modules. The processors may be configured to perform various operations by interpreting machine-readable instructions. Machine-readable instructions may include one or more computer program modules. The computer program modules may include one or more of imaging order module 106, clinical decision support system (CDSS) module 108, notification module 110, and scheduling module 112, and/or other modules.

Server system 102 may store diagnostic imaging order requests within electronic storage 135. A repository of diagnostic imaging orders may be available via server system 102 (e.g., stored within electronic storage 135 and/or other storage location). The repository of diagnostic imaging order requests may be a data structure configured to store information defining diagnostic imaging orders.

Ordering provider 143 may order diagnostic imaging studies for a patient. Ordering provider 143 may be a clinician, a physician, and/or any other professional. Ordering provider 143 may transmit a diagnostic imaging order request to system 102. The diagnostic imaging order requests are transmitted via a communication medium to system 102. The communication medium may comprise a communications network such as a cellular telephone network, a local area network (LAN), a wide area network (WAN), a portion of the Internet, or any combination thereof. A communication medium may be a wireless network system such as a cellular network, a satellite network, a wireless personal area network, a wireless local area network, or other similar communication medium. The medium alternatively may be a wired system, such as a coaxial cable system, a fiber optic cable system, an Ethernet cable system, or other similar communication medium.

The diagnostic imaging order request transmitted by ordering provider 143 may comprise diagnostic imaging order information including one or more data sets associated with at least one of ordering and or referring provider information, patient information, diagnostic imaging order type, and/or clinical decision support information. The request may include one or more identifiers, such as a patient identifier, which may be transmitted to one or more external sources having demographic, insurance information, and/or other information of the patient. The patient information may include other unique information regarding the patient, such as date of birth (DOB), in order to ensure a patient is matched with an insurance payer associated with the patient.

In some implementations, the diagnostic imaging order request may include information including a patient name, a patient identifier, one or more procedure codes, one or more diagnosis codes, a healthcare provider identifier, an insurance payer identifier and/or other information. The information indicating the insurance payer associated with a patient may include an insurance plan name, an insurance member/subscriber name, an insurance member number, an insurance group number, and/or other information.

Imaging order module 106 may receive one or more diagnostic imaging orders transmitted by ordering provider 143 via one or more computing devices. Ordering provider 143 may transmit diagnostic imaging order requests using a standard protocol, such as HL7, DICOM, XML, DICOMWEB, Computerized Physician Order Entry (CPOE) and/or other protocols. For example, as illustrated by FIG. 1, the diagnostic imaging order request may be transmitted as an HL7 Order Message through a web portal to server system 102. In some embodiments, imaging order module 106 may receive one or more diagnostic imaging order requests via a direct entry, direct messaging, email, fax, and/or other submission protocol.

Figure 2:
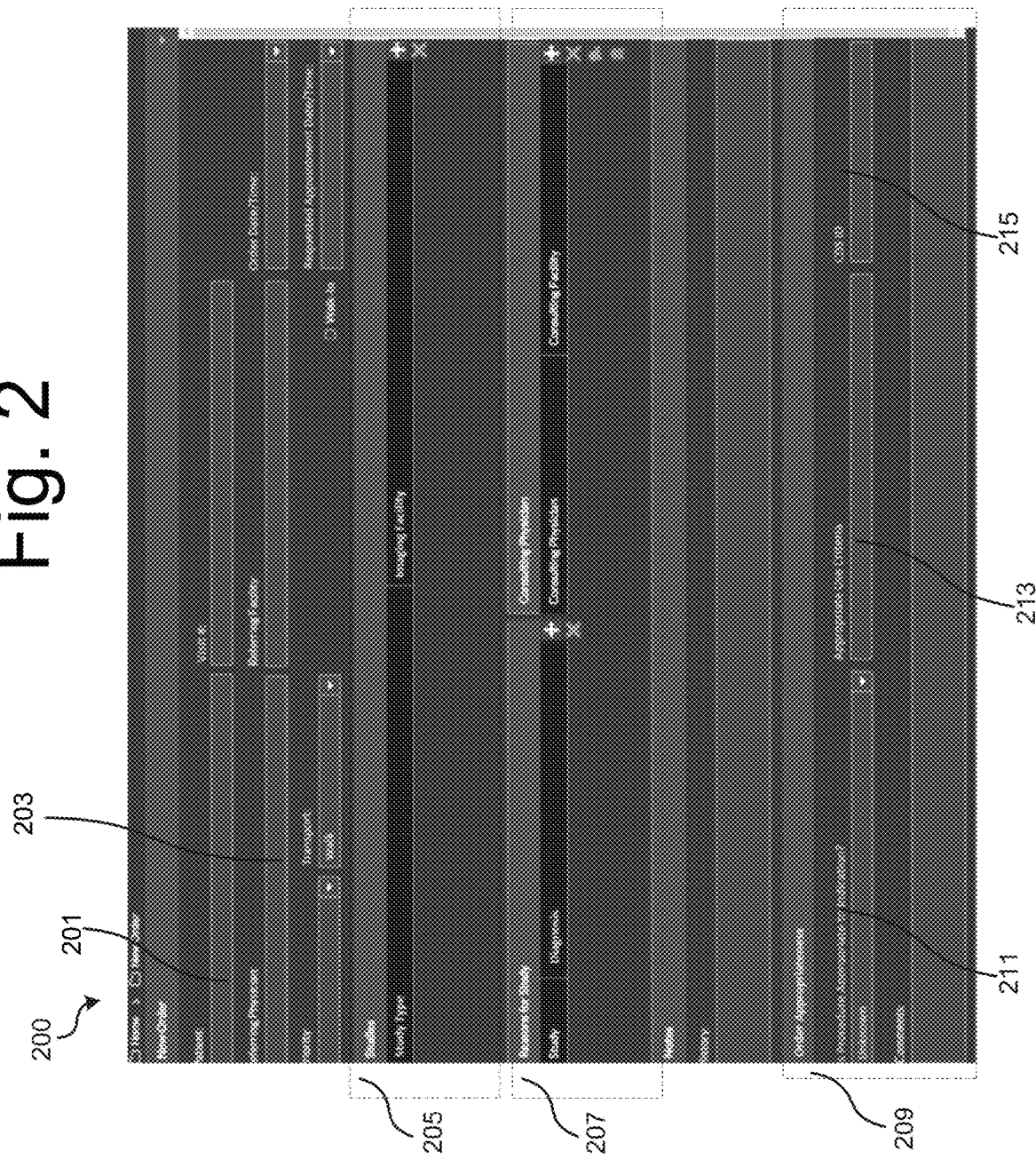
FIG. 2 is a screenshot of graphical user interface showing an entry screen for a diagnostic imaging order, in accordance with one or more implementations

FIG. 2 illustrates an example graphical user interface (GUI) 200 that may be provided for entry of diagnostic imaging order requests. GUI 200 includes a plurality of fields including patient field 201, referring physician field 203, one or more fields 205 associated with requested study type, one or more fields 207 associated with reason for study (diagnosis code), one or more fields 209 associated with order appropriateness, including appropriateness indicator 211, appropriate use criteria consulted 213, a CDS ID 215, a unique ID provided by the CDSS, and/or other fields.

In some embodiments, additional information related to imaging order information may be obtained from one or more external sources and transmitted to system 102. The imaging order request may include one or more identifiers, such as a patient identifier, which may be transmitted to one or more external sources having demographic, insurance payer information, and/or other information of the patient. The patient information may include other unique information regarding the patient, such as date of birth (DOB), to ensure patient can be matched with an insurance payer associated with the patient.

Referring back to FIG. 1, imaging order module 106 may use standard protocols (e.g., HL7, DICOM, FHIR, CCDA, XML) to integrate patient information, provider information, insurance payer information, and/or other data received from disparate systems (examples) to provide a standardized diagnostic imaging order.

Clinical decision support system (CDSS) module 108 may be configured to determine whether ordering provider 143 followed a guideline-based clinical decision support system during the diagnostic imaging order request process. Diagnostic imaging order request received from ordering provider 143 via imaging order module 106 may include clinical decision support information including clinical decision support identifier, appropriate use criteria, and/or other information.

In some implementations, CDSS module 108 may be configured to determine whether a CDSS process is required for diagnostic imaging order for which no CDSS process was consulted. CDSS module 108 may be configured to obtain one or more clinical decision support parameters for determining whether a CDSS is required for the diagnostic imaging order received. One or more clinical decision support parameters may include one or more patient financial classes, one or more insurance payer types, one or more diagnosis codes, one or more imaging study modalities (e.g., CT/MR/PT), and/or other parameters. CDSS module 108 may be configured to obtain one or more clinical decision support parameters by transmitting a request to and obtaining a response from clinical decision support system 127 using standard protocols (e.g., HL7, DICOM, FHIR, CCDA, XML). CDSS module 108 may be configured to determine a CDSS requirement by comparing one or more clinical decision support parameters to imaging order information received by imaging order module 106, such as an insurance payer information associated with the patient, a patient financial class, a diagnosis code, a requested imaging study modality and/or other information. For example, imaging order for an MR imaging study for a patient that has healthcare coverage from a certain insurance payer must be consulted with a clinical decision support system.

Figure 3A:
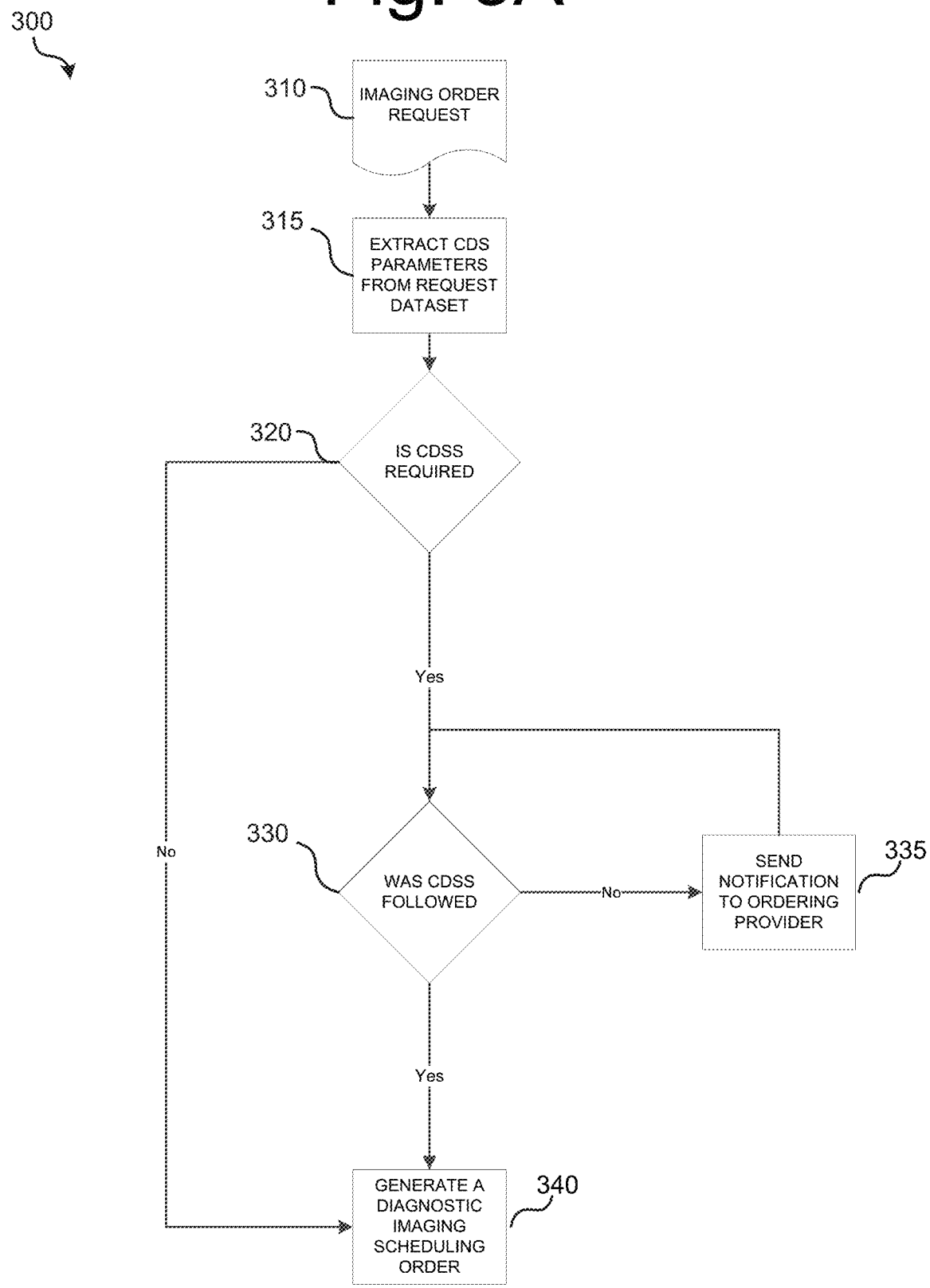
FIG. 3A is an operational flow diagram illustrating an exemplary method of verifying clinical decision support system requirements for diagnostic imaging orders, in accordance with one or more implementations.

FIG. 3A is an operational flow diagram illustrating an exemplary method 300 of managing clinical decision support requirements for diagnostic imaging order requests. In particular implementations, method 300 may be implemented by executing a diagnostic imaging order application (e.g., CDSS module 108 in combination with other software) at server system 102. For example, the application may be provided as a web-based application that is a browser based web application (e.g., interface contained in a web browser) or a client based web application (e.g., client program installed on a local system interacts with application server on the web). Alternatively, in other embodiments the diagnostic imaging order application may be provided as a native-based application.

At operation 310, server system 102 receives and stores diagnostic imaging order requests transmitted by a healthcare provider. In various implementations, the request may include provider information, patient information, diagnostic imaging order information, clinical decision support information, or some combination thereof. In one embodiment, the received diagnostic imaging order requests including diagnostic imaging order information may be stored within electronic storage 135. Electronic storage 135 may comprise one or more local or remote content file servers configured to store diagnostic imaging order request data.

By way of a particular example, the imaging order request may be transmitted as an HL7 message, and the extracted data from the HL7 message may include a diagnostic imaging procedure code, an ordering provider code, an order appropriateness code, a CDSS ID code, payer information, and member identification information. FIG. 3B illustrates an example HL7 Order Message with extracted data fields highlighted. The highlighted extracted data fields are summarized by Table 1, below.

TABLE 1

Data Extracted from an HL7 Order Message

| Field Type | Extracted Data |
|---|---|
| Procedure code | 70100 |
| Ordering Provider NPI | 1234567890 |
| Diagnosis Code | 830.1 |
| Order Appropriateness Indicator | 76515-6 |
| CDSS ID | 1.2.840.5677912.434.56.78.8.9.0.1223 |
| Payer | BCBS |
| Member ID | G412343 |

At operation 315, server system 102 extracts one or more clinical decision support parameters for determining whether a CDSS process is required for the diagnostic imaging order. The clinical decision support parameters may comprise selected diagnoses (e.g., based on a diagnosis code), selected payers, and/or other information.

At decision 320, server system 102 determines whether CDSS is required. For example, CDSS module 108 may receive extracted clinical decision support parameters and determine whether the diagnostic imaging order requires to follow a CDSS process based on these parameters. In some implementations, CDSS module 108 may be configured to determine whether a diagnosis code is associated with an imaging order request corresponds to a set of priority clinical areas defined as clinical conditions, diseases or symptom complexes. For example, clinical conditions such as coronary artery disease (suspected or diagnosed), suspected pulmonary embolism, headache (traumatic and non-traumatic), hip pain, low back pain, shoulder pain (to include suspected rotator cuff injury), cancer of the lung (primary or metastatic, suspected or diagnosed), cervical or neck pain have been identified to require a CDSS process during imaging order request. CDSS module 108 may be configured to obtain a set of conditions, diseases or symptom complexes and transform them into ICD-10 diagnosis codes and/or other formats. CDSS module 108 may be configured to obtain a diagnosis code received by imaging order module 106 and compare it to the transformed diagnosis code corresponding to the priority clinical areas. In the example of FIG. 3B, the diagnosis code associated with the imaging order was 830.1^DISLOCATION OF JAW; OPEN DISLOCATION, so in this case, a CDSS process may not be required.

By way of particular example, if the extracted data from an HL7 message indicates that the patient is a Medicare patient and a CT, MR, or PET scan is ordered, at decision 320 it may be determined that CDSS is required. Conversely if the extracted data indicates that the patient is an ER patient, at decision 320 it may be determined that CDSS is not required. In the example in FIG. 3B, the patient was a BOBS patient and an X-RAY was ordered, so in this case, a CDSS process may not be required.

If CDSS is not required, at operation 340 a diagnostic imaging scheduling order may be generated. Otherwise, at decision 330, upon determining that an imaging order associated with an imaging order request meets the requirements to follow a CDSS process, CDSS module 108 may determine whether ordering provider 143 followed a guideline-based clinical decision support system. Server system 102 receives clinical decision support information including one or more clinical decision support identifiers for determining whether a CDSS process was followed by an ordering physician for the diagnostic imaging order. In the example in FIG. 3B, the Order Appropriateness indicator 76515-6 indicates that CDSS process was followed and confirmed that the requested imaging procedure code 70100 is appropriate to the patient's diagnosis code 830.1.

If CDSS was followed, a diagnostic imaging scheduling order may be generated at operation 340. Otherwise, at operation 335, server system 102 sends an electronic notification to ordering provider 143 upon determining that an imaging order request requires a CDSS process that ordering provider 143 did not follow.

Referring back to FIG. 1, notification module 110 may be configured to notify ordering physicians that a decision support process required for the imaging order transmitted was not followed. The notification may be sent using a direct messaging protocol, a text message, an email, and/or other type of communication protocol. In some implementations, notification module 110 may be configured to send notification through conventional distribution channels. For example, the notification may be delivered by calling the physician directly, distributing the notification via facsimile, and/or other by using delivery methods. For example, if the notification is distributed via facsimile, the notification may include a barcode such as a QR code with an embedded file path for accessing a clinical diagnostic support system associated with a diagnostic imaging order request, and/or other information.

In some implementations, notification module 110 may be configured to generate a notification using ordering provider 143 information contained in an imaging ordering request received by imaging order module 106. In some implementations, additional information related to ordering provider 143 may be obtained from one or more external sources (e.g., CMS, National Physician Identifier Registry, Sure-Scripts directory) and transmitted to system 102. For example, the imaging order request may include one or more ordering physician identifiers which may be transmitted to one or more external sources having name, address, phone number, fax number, email address, and/or other information of the physician.

A notification generated by notification module 110 may include imaging order information (e.g., patient name, imaging study modality, imaging facility, diagnosis code, etc.), clinical decision support system information, a file path access information (e.g. login/password, encryption key, etc.) for accessing the clinical decision support system at the associated file path, and/or other information.

Figure 4:
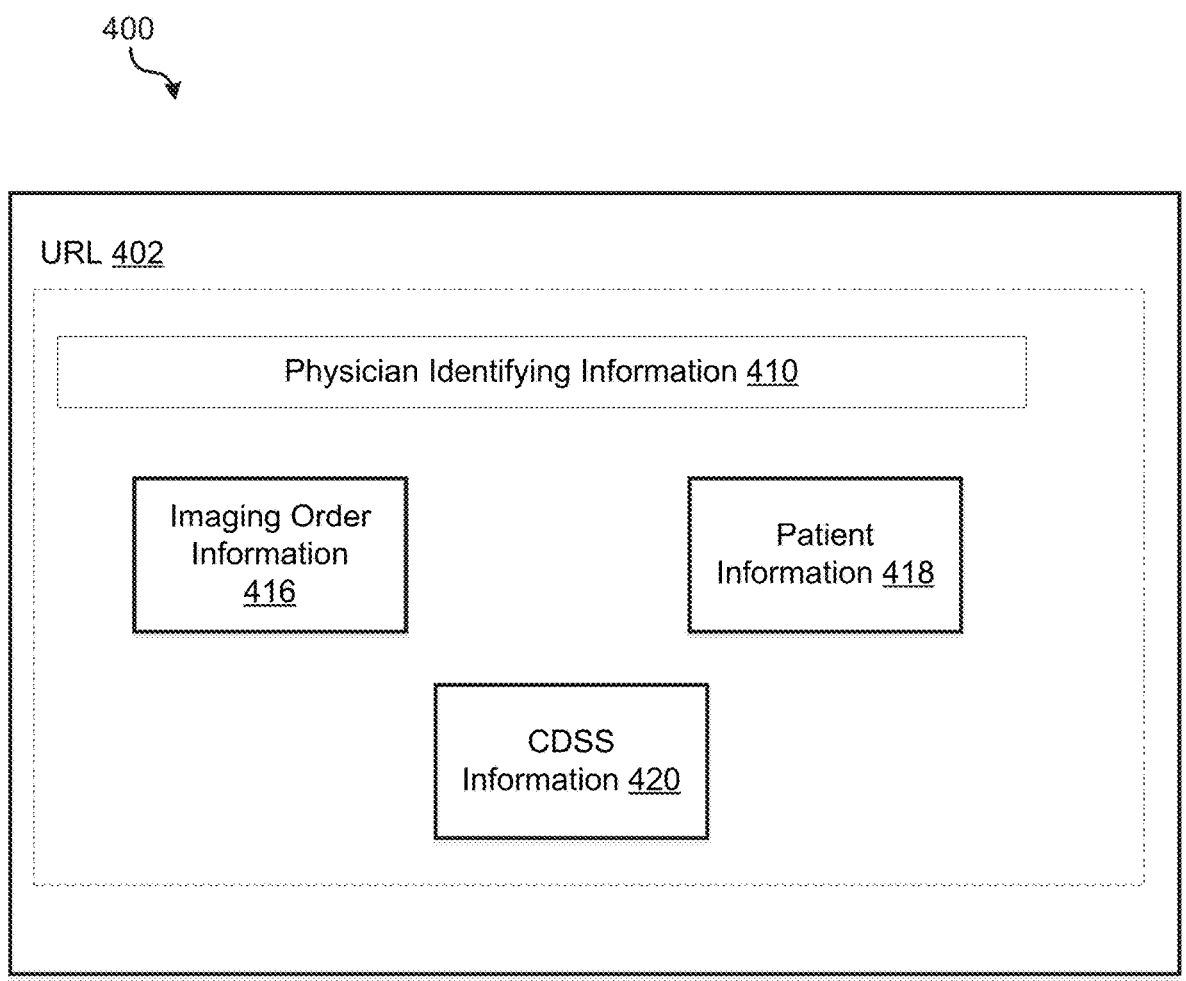
FIG. 4 is an example notification to an ordering provider, in accordance with one or more implementations.

The file path may be a URL for accessing clinical diagnostic support system associated with a diagnostic imaging order request. For example, and as illustrated in FIG. 4, notification 400 may include a URL 402 for accessing clinical diagnostic support system associated with a diagnostic imaging order request, physician identifying information 410, imaging order information 416, and CDSS information 420. In implementations, the URL may be a shortened form of the actual URL generated using a URL shortening service. Construction of the shortened URL may follow predefined rules. As another example, the URL may be constructed as to avoid any reference to patient demographic information in the URL to avoid transmitting any unencrypted Protected Health Information (PHI) across the Internet. In the described embodiments, the URL may use the Hypertext Transfer Protocol Secure (HTTPS) protocol. In one embodiment, notifications may include clickable file paths, thereby allowing immediate access to a clinical diagnostic support system.

In implementations, notification module 110 may be configured to use any number of authentication methods for authenticating a client computing device that receives the notifications and access CDSS. For example, it may use password authentication, digital signature authentication, IP SEC authentication, Transport Layer (TLS) authentication, Secure Sockets Layer (SSL) authentication, public-key cryptography authentication, etc. In response to the notification, server system 102 may receive clinical decision support information including one or more clinical decision support identifiers from ordering provider 143.

Scheduling module 112 may be configured to generate diagnostic imaging scheduling orders in response to diagnostic imaging order requests transmitted by ordering provider 143. Diagnostic imaging scheduling orders may be configured to include diagnostic imaging order information such referring provider information, patient information, diagnostic imaging order type, one or more procedure codes, one or more diagnosis codes, a healthcare provider identifier, an insurance payer, clinical decision support information, scheduling order parameters such as date, time, location, and/or other information. Diagnostic imaging scheduling orders may be transmitted to order scheduling department 123 of imaging facility 120 using standard protocols (e.g., HL7, DICOM, FHIR, CCDA, XML). Scheduling module 112 may be configured to accept responses from order placer 121 of imaging facility 120 using standard protocols. Responses from order placer 121 may include scheduling confirmation, scheduling information, including such as date, time, and imaging facility information, patient recommendations, and/or other information.

For example, as illustrated in FIG. 3A, upon determining that CDSS was followed at decision 330, server system 102 may be configured to generate a diagnostic imaging scheduling order at operation 340 (e.g., using scheduling module 112). The diagnostic imaging scheduling order may include imaging order information received by imaging order module 106, clinical decision support information obtained by imaging order module 106, CDSS module 108, and/or notification module 110. Scheduling module 112 may be configured to transmit the diagnostic imaging scheduling order to scheduling department 123 within imaging facility 120.

Referring back to FIG. 1, In some implementations, system 102 may be configured to determine insurance eligibility requirements. System 102 may be configured to determine insurance eligibility requirements using an insurance module and/or other module. System 102 may be configured to determine insurance eligibility requirements by transmitting a request to and obtaining a response from insurance eligibility system 125 using standard protocols (e.g., HL7, DICOM, FHIR, CCDA, XML).

Figure 3C:
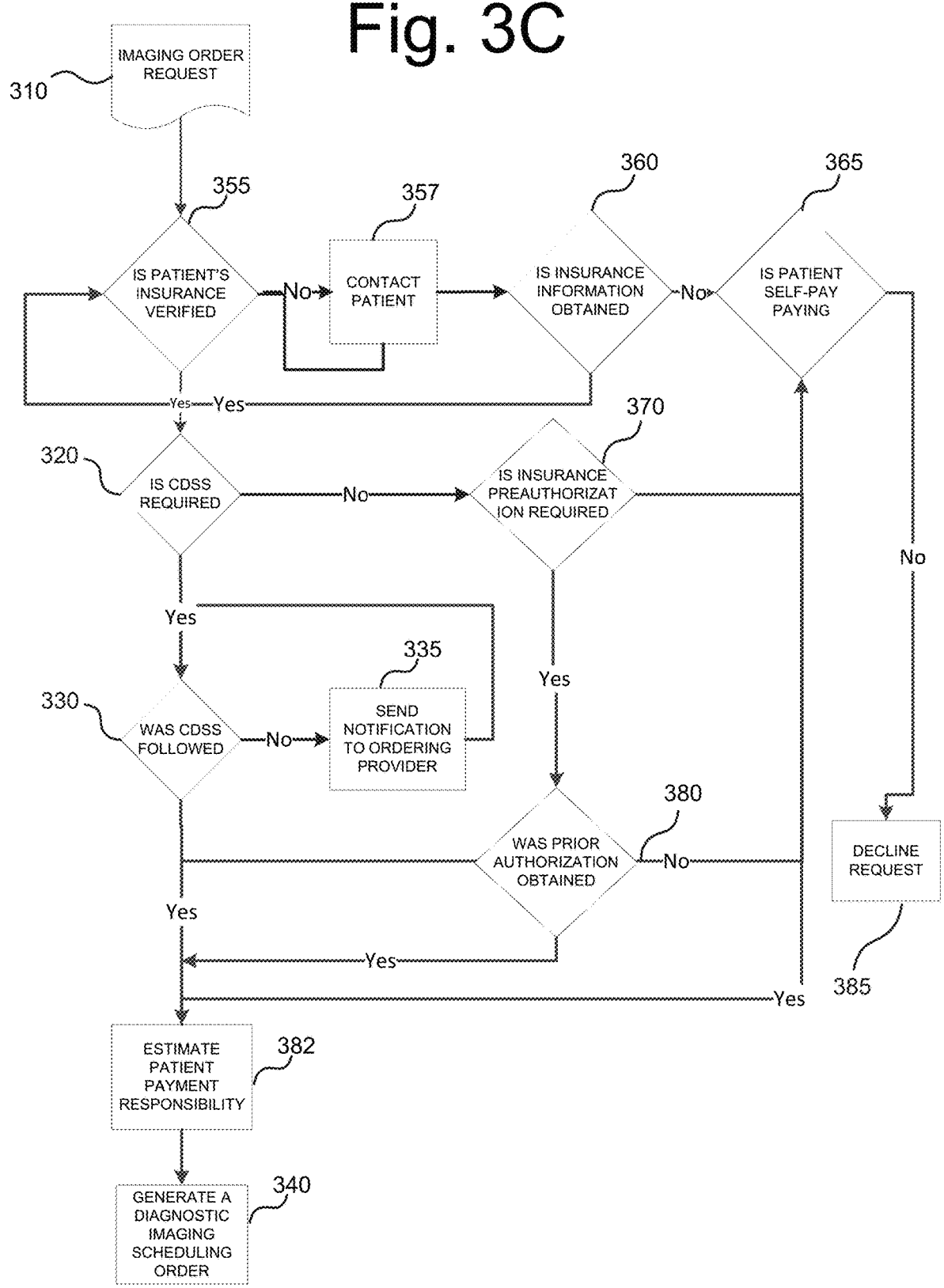
FIG. 3C is an operational flow diagram illustrating an exemplary method of managing diagnostic imaging orders, in accordance with one or more implementations.

For example, and as illustrated in FIG. 3C, method 300 may be incorporated into a process that further determines if a patient is insured and if insurance preauthorization is required. In one such implementation, system 102 may determine whether insurance payer preauthorization is required for the diagnostic imaging order received. One or more preauthorization parameters may be used including one or more patient financial classes, one or more insurance payer types, one or more diagnosis codes, one or more imaging study modalities (e.g., CT/MR/PT), and/or other parameters.

At decision 355, upon determining that a patient's insurance payer has not been verified, server system 102 may be configured to contact the patient at operation 357 to verify insurance payer information. At operation 357, the patient may be contacted by system 102 using direct messaging, email, fax, and/or other communication protocol.

At decision 360, upon determining that patient insurance information was not obtained, server system 102 may be configured to determine if patient is personally responsible for payment. At decision 365, upon determining that patient is not personally responsible for payment, server system 102 may decline the diagnostic imaging order request at operation 385. Conversely, upon determining that patient is personally responsible for payment associated with the order request, server system 102 may generate a diagnostic imaging scheduling order at operation 340 (e.g., using scheduling module 112).

At decision 320, upon determining that CDSS is not required, server system 102 may be configured to determine if insurance preauthorization is required. At decision 370, upon determining that insurance preauthorization is required, server system 102 may be configured to determine whether prior insurance authorization was obtained. At decision 380, upon determining that insurance preauthorization was not obtained, server system 102 may decline the diagnostic imaging order request at operation 385. Alternatively, if insurance preauthorization was obtained, server system 102 may generate a diagnostic imaging scheduling order at operation 340 (e.g., using scheduling module 112). In yet further implementations, prior to generating the diagnostic imaging scheduling order at operation 340, server system 102 may be configured to estimate patient payment responsibility at operation 382. As illustrated in FIG. 1, patient 141 may access system 102 via a client computing platform to view the estimate. In some implementations, system 102 may be configured to include a web-portal and/or other application accessible by patients. In yet further implementations, server system 102 may generate and deliver the estimate directly to patient 141 using direct messaging, email, fax, and/or other communication protocol.

In yet further implementations, system 102 may track historical statistics relating to CDSS compliance by ordering provider 143, CDSS compliance by healthcare group, and other like information.

Figure 5:
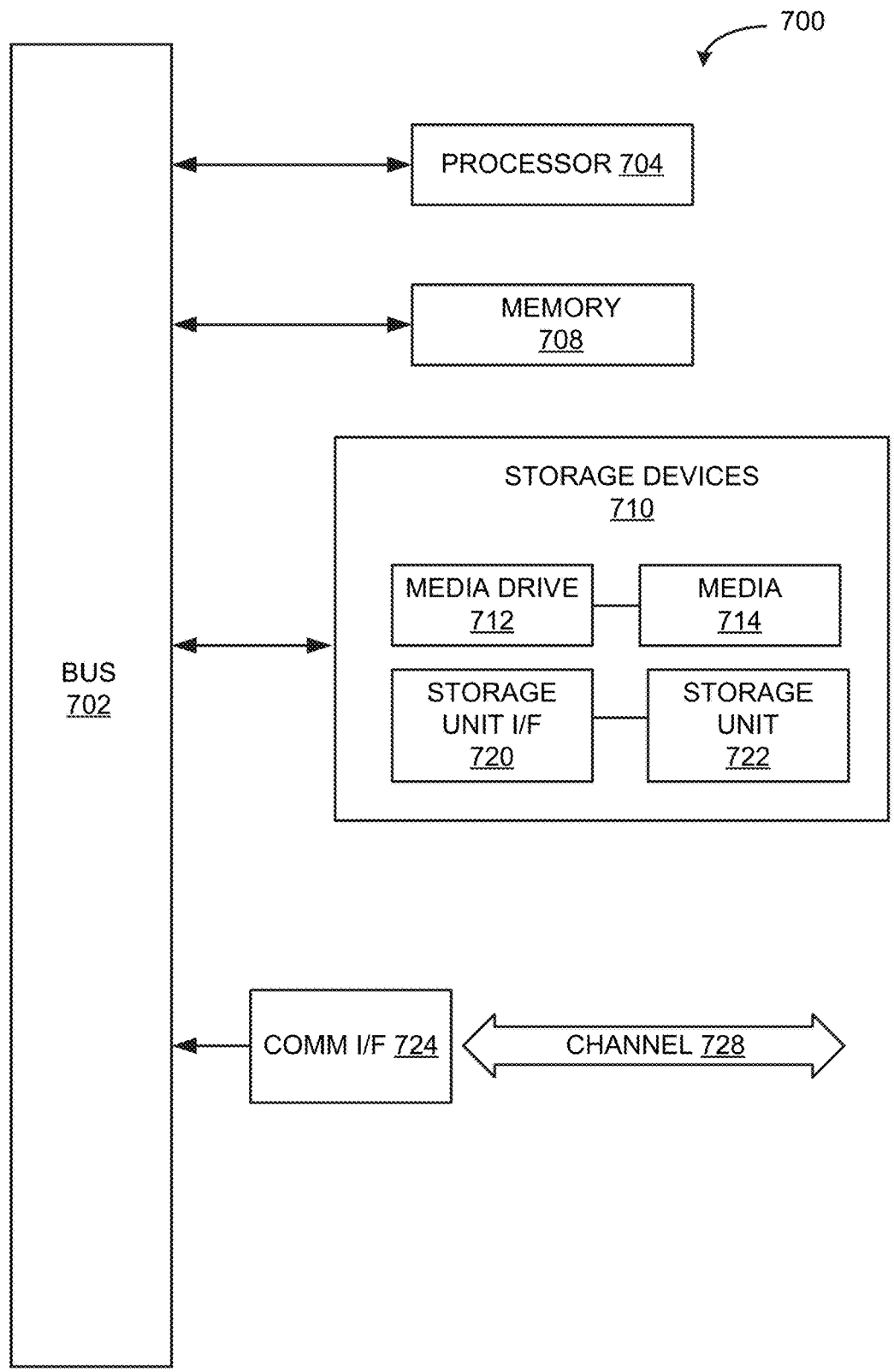
FIG. 5 is an example computing module that may be used to implement various features of the systems and methods disclosed herein.

FIG. 5 illustrates an example computing module that may be used to implement various features of the system and methods disclosed herein, such as the aforementioned features and functionality of one or more aspects of imaging order module 106, CDSS module 108, notification module 110, scheduling module 112, and server system 102.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 5. Various embodiments are described in terms of this example-computing module 700. After reading this description, it will become apparent to a person skilled in the relevant art how to implement the application using other computing modules or architectures.

Referring now to FIG. 5, computing module 700 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. Computing module 700 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 700 might include, for example, one or more processors, controllers, control modules, or other processing devices, such as a processor 704. Processor 704 might be implemented using a general-purpose or special-purpose processing engine such as, for example, a microprocessor, controller, or other control logic. In the illustrated example, processor 704 is connected to a bus 702, although any communication medium can be used to facilitate interaction with other components of computing module 700 or to communicate externally.

Computing module 700 might also include one or more memory modules, simply referred to herein as main memory 708. For example, preferably random access memory (RAM) or other dynamic memory, might be used for storing information and instructions to be executed by processor 704. Main memory 708 might also be used for storing temporary variables or other intermediate information during execution of instructions to be executed by processor 704. Computing module 700 might likewise include a read only memory ("ROM") or other static storage device coupled to bus 702 for storing static information and instructions for processor 704.

The computing module 700 might also include one or more various forms of information storage mechanism 710, which might include, for example, a media drive 712 and a storage unit interface 720. The media drive 712 might include a drive or other mechanism to support fixed or removable storage media 714. For example, a hard disk drive, a solid state drive, a magnetic tape drive, an optical disk drive, a CD or DVD drive (R or RW), or other removable or fixed media drive might be provided. Accordingly, storage media 714 might include, for example, a hard disk, a solid state drive, magnetic tape, cartridge, optical disk, a CD, DVD, or Blu-ray, or other fixed or removable medium that is read by, written to or accessed by media drive 712. As these examples illustrate, the storage media 714 can include a computer usable storage medium having stored therein computer software or data.

In alternative embodiments, information storage mechanism 710 might include other similar instrumentalities for allowing computer programs or other instructions or data to be loaded into computing module 700. Such instrumentalities might include, for example, a fixed or removable storage unit 722 and an interface 720. Examples of such storage units 722 and interfaces 720 can include a program cartridge and cartridge interface, a removable memory (for example, a flash memory or other removable memory module) and memory slot, a PCMCIA slot and card, and other fixed or removable storage units 722 and interfaces 720 that allow software and data to be transferred from the storage unit 722 to computing module 700.

Computing module 700 might also include a communications interface 724. Communications interface 724 might be used to allow software and data to be transferred between computing module 700 and external devices. Examples of communications interface 724 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 724 might typically be carried on signals, which can be electronic, electromagnetic (which includes optical) or other signals capable of being exchanged by a given communications interface 724. These signals might be provided to communications interface 724 via a channel 728. This channel 728 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer readable medium", "computer usable medium" and "computer program medium" are used to generally refer to non-transitory media, volatile or non-volatile, such as, for example, memory 708, storage unit 722, and media 714. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 700 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

What is claimed is:

1. A system of managing diagnostic imaging orders, the system comprising:
   a processor;
   a memory coupled to the processor, wherein the memory stores a set of instructions configured to cause the processor to:
      receive a diagnostic imaging order, the diagnostic imaging order comprising ordering provider information, patient information, diagnostic imaging order information, and clinical decision support information, the clinical decision support information including a first clinical decision support identifier;
      extract at least one clinical decision support parameter from the clinical decision support information;
      determine whether following a clinical decision support process for the diagnostic imaging order is required using at least the extracted clinical decision support parameter;
      in response to determining that following the clinical decision support process for the diagnostic imaging order is required, using at least the first clinical decision support identifier to determine if the clinical decision support process was followed for the diagnostic imaging order by an ordering provider;
      upon determining that the clinical decision support process for the diagnostic imaging order was not followed, generate a notification by extracting the ordering provider information, the patient information, the diagnostic imaging order information, and the clinical decision support information from the received diagnostic imaging order, wherein the generated notification comprises a barcode comprising an embedded file path to a file server storing clinical decision support information, and wherein access to the clinical decision support information on the file server requires access rights comprising at least one or more authentication parameters, wherein the embedded file path is a shortened Uniform Resource Locator (URL) constructed from an original URL and comprises the one or more authentication parameters for accessing the clinical decision support information at the embedded file path;
      transmit the notification, via a web-based graphical user interface (GUI), to the ordering provider;
      receive a response from the ordering provider indicating that the clinical decision support process has been performed, wherein the ordering provider sends the response by scanning the barcode of the transmitted notification to access the clinical decision support information using the one or more authentication parameters stored within the barcode at the embedded file path;
      modify the first clinical decision support identifier based on the response from the ordering provider;
      obtain a second clinical decision support identifier comprising a modified first clinical decision support identifier; and
      generate a scheduling order.

2. The system of claim 1, wherein the extracted clinical decision support parameter comprises a diagnosis code, wherein determining whether following the clinical decision support process for the diagnostic imaging order is required comprises determining whether the diagnosis code corresponds to a set of priority clinical areas defined as clinical conditions, diseases or symptom complexes.

3. The system of claim 1, wherein the notification is transmitted to the ordering provider via a communication protocol, the communication protocol comprising at least one of a text message, an email, and a direct message, and wherein the notification comprises notification information generated by extracting the ordering provider information, the patient information, the diagnostic imaging order information, and the clinical decision support information from the received diagnostic imaging order.

4. The system of claim 1, wherein the diagnostic imaging order request comprises an HL7 message, the HL7 message comprising a one or more data fields including at least one of a diagnostic image procedure code, an ordering provider code, an order appropriateness code, a CDSS ID code, payer information, and member identification information.

5. The system of claim 4, wherein the ordering provider information, the patient information, the diagnostic imaging order information, and the clinical decision support information are extracted from the one or more data fields of the HL7 message.

6. The system of claim 4, further comprising determining whether following the clinical decision support process for the diagnostic imaging order is required based on the order appropriateness code.

7. The system of claim 4, the clinical decision support information specifying whether an ordering provider has performed a clinical decision support procedure for the diagnostic imaging order is extracted from the CDSS ID code data field of the HL7 message.

8. The system of claim 1, wherein the scheduling order comprises scheduling order information comprising at least one of the ordering provider information, the patient information, the diagnostic imaging order information, and the clinical decision support information, wherein the ordering provider information, the patient information, the diagnostic imaging order information, and the clinical decision support information are extracted from the diagnostic imaging order.

9. A non-transitory computer readable storage medium comprising a set of instructions executable by at least one processor resource to:
receive a diagnostic imaging order, the diagnostic imaging order comprising ordering provider information, patient information, diagnostic imaging order information, and clinical decision support information, the clinical decision support information including a first clinical decision support identifier, the first clinical decision support identifier specifying whether an ordering provider has performed a clinical decision support procedure for the diagnostic imaging order;
responsive to the clinical decision support procedure not performed indicated by the first clinical decision support identifier, then
obtain at least one clinical decision support parameter from a clinical decision support server;
determine whether following the clinical decision support process for the diagnostic imaging order is required based on the at least one clinical decision support parameter;
upon determining that the clinical decision support process for the diagnostic imaging order was not followed, generate a notification by extracting the ordering provider information, the patient information, the diagnostic imaging order information, and the clinical decision support information from the received diagnostic imaging order, wherein the generated notification comprises a barcode comprising an embedded file path to a file server storing clinical decision support information, and wherein access to the clinical decision support information on the file server requires access rights comprising at least one or more authentication parameters, wherein the embedded file path is a shortened Uniform Resource Locator (URL) constructed from an original URL and comprises the one or more authentication parameters for accessing the clinical decision support information at the embedded file path;
transmit the notification, via a web-based graphical user interface (GUI), to the ordering provider;
receive a response from the ordering provider indicating that the clinical decision support procedure has been performed, wherein the ordering provider sends the response by scanning the barcode of the transmitted notification to access the clinical decision support information using the one or more authentication parameters stored within the barcode at the embedded file path;
modify the first clinical decision support identifier based on the response from the ordering provider;
obtain a second clinical decision support identifier comprising a modified first clinical decision support identifier; and
generate a scheduling order.

10. The non-transitory computer readable storage medium of claim 9, wherein the set of instructions are executable by the at least one processor resource to determine whether following the clinical decision support process for the diagnostic imaging order is required comprising:
extracting a diagnostic code from the diagnostic imaging order information;
generating an ICD-10 diagnostic code based on the extracted diagnostic code;
receiving a priority clinical area identifier based on the ICD-10 diagnostic code; and
using the priority clinical area identifier to determine whether following the clinical decision support process for the diagnostic imaging order is required.

11. The non-transitory computer readable storage medium of claim 9, wherein the notification is transmitted to the ordering provider via a communication protocol, the communication protocol comprising at least one of a text message, an email, and a direct message, and wherein the notification comprises notification information, the notification information being generated by extracting the ordering provider information, the patient information, the diagnostic imaging order information, and the clinical decision support information from the received diagnostic imaging order.

12. A method of managing diagnostic imaging orders, the method being implemented by a computing system including one or more physical processors and storage media storing machine-readable instructions, the method comprising:
receiving a diagnostic imaging order, the diagnostic imaging order comprising diagnostic imaging order information including ordering provider information, patient information, diagnostic imaging order information, and clinical decision support information, the clinical decision support information including a first clinical decision support identifier, the first clinical decision support identifier specifying whether an ordering provider has followed a clinical decision support process for the diagnostic imaging order;

if the ordering provider has not performed the clinical decision support process associated with the diagnostic imaging order, then obtaining, by a clinical decision support server, at least one clinical decision support parameter;

determining whether following the clinical decision support process for the diagnostic imaging order is required based on the at least one clinical decision support parameter;

upon determining that the clinical decision support process for the diagnostic imaging order was not followed, generating a notification by extracting the ordering provider information, the patient information, the diagnostic imaging order information, and the clinical decision support information from the received diagnostic imaging order, wherein the generated notification comprises a barcode comprising an embedded file path to a file server storing clinical decision support information, and wherein access to the clinical decision support information on the file server requires access rights comprising at least one or more authentication parameters, wherein the embedded file path is a shortened Uniform Resource Locator (URL) constructed from an original URL and comprises the one or more authentication parameters for accessing the clinical decision support information at the embedded file path;

providing a web-based interface for transmitting the notification to the ordering provider;

receiving a response from the ordering provider indicating that the clinical decision support procedure has been performed, wherein the ordering provider sends the response by scanning the barcode of the transmitted notification to access the clinical decision support information using the one or more authentication parameters stored within the barcode at the embedded file path;

modifying the first clinical decision support identifier based on the ordering provider response;

obtaining a second clinical decision support identifier comprising a modified first clinical decision support identifier; and generating a scheduling order.

13. The method of claim 12, wherein the diagnostic imaging order is received via at least one of a HL7 protocol, a DICOM protocol, a DICOMWEB protocol, an XML protocol, and a Computerized Physician Order Entry (CPOE) protocol.

14. The method of claim 12, wherein the diagnostic imaging order information comprises a diagnostic code.

15. The method of claim 14, further comprising generating an ICD-10 diagnostic code based on the diagnostic code.

16. The method of claim 15, further comprising receiving a priority clinical area identifier based on the ICD-10 diagnostic code.

17. The method of claim 16, further comprising determining whether following the clinical decision support process for the diagnostic imaging order is required based on the priority clinical area identifier.

18. The method of claim 12, wherein the at least one clinical decision support parameter includes one of a patient financial class, an insurance payer type, a diagnostic code, and an imaging study modality.

19. The method of claim 12, wherein determining whether following the clinical decision support process for the diagnostic imaging order is required comprises comparing the diagnostic imaging order information to the at least one clinical decision support parameter.

20. The method of claim 12, wherein the notification is transmitted to the ordering provider via a communication protocol, the communication protocol comprising at least one of a text message, an email, and a direct message.

* * * * *